(12) United States Patent
Alvarez-Carrigan et al.

(10) Patent No.: US 7,416,737 B2
(45) Date of Patent: Aug. 26, 2008

(54) ANTIMICROBIAL LENSES, PROCESSES TO PREPARE THEM AND METHODS OF THEIR USE

(75) Inventors: Nayiby Alvarez-Carrigan, St. Augustine, FL (US); Susan Brown-Skrobot, Jacksonville, FL (US); Ann-Marie Wong Meyers, Jacksonville, FL (US); Frank Neely, Jacksonville, FL (US); Brian Pall, Jacksonville, FL (US); Osman Rathore, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 242 days.

(21) Appl. No.: 10/882,072

(22) Filed: Jun. 30, 2004

(65) Prior Publication Data

US 2005/0117112 A1    Jun. 2, 2005

Related U.S. Application Data

(63) Continuation-in-part of application No. 10/715,903, filed on Nov. 18, 2003.

(51) Int. Cl.
*A61K 6/08* (2006.01)

(52) U.S. Cl. ............... 424/409; 351/160 R; 424/429; 424/618; 424/421; 424/617; 523/106

(58) Field of Classification Search .............. 523/106; 525/101, 903; 424/429, 618, 409, 421, 617; 351/160 R
See application file for complete search history.

(56) References Cited

U.S. PATENT DOCUMENTS

| | | | |
|---|---|---|---|
| 3,808,178 A | 4/1974 | Gaylord | |
| 4,120,570 A | 10/1978 | Gaylord | |
| 4,136,250 A | 1/1979 | Mueller | |
| 4,139,513 A | 2/1979 | Tanaka et al. | |
| 4,139,692 A | 2/1979 | Tanaka et al. | |
| 4,153,641 A | 5/1979 | Deichert et al. | |
| 4,182,822 A | 1/1980 | Chang | |
| 4,189,546 A | 2/1980 | Deichert et al. | |
| 4,254,248 A | 3/1981 | Friends et al. | |
| 4,259,467 A | 3/1981 | Keogh et al. | |
| 4,260,725 A | 4/1981 | Keogh et al. | |
| 4,261,875 A | 4/1981 | LeBoeuf | |
| 4,276,402 A | 6/1981 | Chromecek et al. | |
| 4,304,012 A | 12/1981 | Richard | |
| 4,327,203 A | 4/1982 | Deichert et al. | |
| 4,330,383 A | 5/1982 | Ellis et al. | |
| 4,341,889 A | 7/1982 | Deichert et al. | |
| 4,343,927 A | 8/1982 | Chang | |
| 4,355,147 A | 10/1982 | Deichert et al. | |
| 4,450,264 A | 5/1984 | Cho | |
| 4,463,149 A | 7/1984 | Ellis | |
| 4,486,577 A | 12/1984 | Mueller et al. | |
| 4,525,563 A | 6/1985 | Shibata et al. | |
| 4,543,398 A | 9/1985 | Bany et al. | |
| 4,605,712 A | 8/1986 | Mueller et al. | |
| 4,661,575 A | 4/1987 | Tom | |
| 4,703,097 A | 10/1987 | Wingler et al. | |
| 4,711,943 A | 12/1987 | Harvey, III | |
| 4,725,277 A | 2/1988 | Bissonette | |
| 4,731,079 A | 3/1988 | Stoy | |
| 4,837,289 A | 6/1989 | Mueller et al. | |
| 4,863,464 A | 9/1989 | Dusek | |
| 4,871,785 A | 10/1989 | Froix | |
| 4,872,876 A | 10/1989 | Smith | |
| 4,954,586 A | 9/1990 | Toyochima et al. | |
| 4,954,587 A | 9/1990 | Mueller | |
| 4,973,493 A | 11/1990 | Guire | |
| 5,006,622 A | 4/1991 | Kunzler et al. | |
| 5,010,141 A | 4/1991 | Mueller | |
| 5,034,461 A | 7/1991 | Lai et al. | |
| 5,057,578 A | 10/1991 | Spinelli | |
| 5,070,215 A | 12/1991 | Bambury et al. | |
| 5,135,297 A | 8/1992 | Valint, Jr. | |
| 5,256,751 A | 10/1993 | Vanderlaan | |
| 5,275,838 A | 1/1994 | Merrill | |
| 5,311,223 A | 5/1994 | Vanderlaan | |
| 5,314,960 A | 5/1994 | Spinelli et al. | |
| 5,336,797 A | 8/1994 | McGee et al. | |
| 5,346,946 A | 9/1994 | Yokoyama et al. | |
| 5,358,995 A | 10/1994 | Lai et al. | |
| 5,371,147 A | 12/1994 | Spinelli et al. | |
| 5,387,632 A | 2/1995 | Lai et al. | |
| 5,451,617 A | 9/1995 | Lai et al. | |
| 5,486,579 A | 1/1996 | Lai et al. | |
| 5,520,910 A * | 5/1996 | Hashimoto et al. ........ 424/78.31 |
| 5,710,302 A | 1/1998 | Kunzler et al. | |
| 5,714,557 A | 2/1998 | Kunzler et al. | |
| 5,760,100 A | 6/1998 | Nicolson et al. | |
| 5,776,999 A | 7/1998 | Nicolson et al. | |
| 5,779,943 A | 7/1998 | Enns et al. | |
| 5,789,461 A | 8/1998 | Nicolson et al. | |
| 5,807,944 A | 9/1998 | Hirt et al. | |
| 5,849,811 A | 12/1998 | Nicolson et al. | |
| 5,908,906 A | 6/1999 | Kunzler et al. | |

(Continued)

FOREIGN PATENT DOCUMENTS

EP        406161 B1        2/1995

(Continued)

OTHER PUBLICATIONS

PCT International Search Report, dated Sep. 15, 2005, for PCT Int'l. Appln. No. PCT/US2005/021077.

(Continued)

*Primary Examiner*—Peter D. Mulcahy
*Assistant Examiner*—Henry Hu

(57) ABSTRACT

This invention relates to solutions for packaging ophthalmic devices comprising at least one antimicrobial metal salt which prevent the loss of said antimicrobial metal salt during autoclaving and storage.

11 Claims, No Drawings

U.S. PATENT DOCUMENTS

| | | | |
|---|---|---|---|
| 5,944,853 A | 8/1999 | Molock et al. | |
| 5,958,440 A | 9/1999 | Burrell et al. | |
| 5,962,548 A | 10/1999 | Vanderlaan | |
| 5,965,631 A | 10/1999 | Nicolson et al. | |
| 5,981,615 A | 11/1999 | Meijs et al. | |
| 5,981,675 A | 11/1999 | Valint, Jr. et al. | |
| 5,998,498 A | 12/1999 | Vanderlaan et al. | |
| 6,020,445 A | 2/2000 | Vanderlaan et al. | |
| 6,039,913 A | 3/2000 | Hirt et al. | |
| 6,087,415 A | 7/2000 | Vanderlaan et al. | |
| 6,193,369 B1 | 2/2001 | Valint, Jr. et al. | |
| 6,200,626 B1 | 3/2001 | Grobe, III et al. | |
| 6,213,604 B1 | 4/2001 | Valint, Jr. et al. | |
| 6,367,929 B1 | 4/2002 | Maiden et al. | |
| 6,815,074 B2 * | 11/2004 | Aguado et al. | 428/447 |
| 2002/0016383 A1 | 2/2002 | Iwata et al. | |
| 2003/0095230 A1 | 5/2003 | Neely et al. | |
| 2004/0115242 A1 * | 6/2004 | Meyers et al. | 424/429 |
| 2004/0151755 A1 * | 8/2004 | Rathore et al. | 424/429 |

FOREIGN PATENT DOCUMENTS

| | | |
|---|---|---|
| JP | 2000016905 | 7/1998 |
| JP | 2001-183502 | 7/2001 |
| JP | 2001-188101 | 7/2001 |
| JP | 2001-201723 | 7/2001 |
| JP | 2002-327063 | 11/2002 |
| WO | WO 94/21698 A1 | 9/1994 |
| WO | WO 99/27978 A1 | 6/1999 |
| WO | WO 99/29750 A1 | 6/1999 |
| WO | WO 00/22459 A1 | 4/2000 |
| WO | WO 00/22460 A1 | 4/2000 |
| WO | WO 00/26698 A1 | 5/2000 |
| WO | WO 03/011351 A2 | 2/2003 |
| WO | WO 03/011551 A1 | 2/2003 |
| WO | WO 03/022321 A2 | 3/2003 |
| WO | WO 2004/047879 | 6/2004 |
| WO | WO-2004/047879 A2 * | 6/2004 |

OTHER PUBLICATIONS

U.S. Appl. No. 09/532,943, filed Mar. 22, 2000, Margiss et al.

CRC Handbook of Chemistry and Physics, 78$^{th}$ Edition, CRC Press, Boca Raton Florida, 1997-99, pp. 8-106 through 8-109).

Encyclopedia of Polymer Science and Engineering, N-Vinyl Amide Polymers, Second edition, vol. 17, pp. 198-257, John Wiley & Sons Inc.

Becker, D. A.; Greenberg, R.R.; Stone, S. F. J. Radioanal. Nucl. Chem. 1992, 160(1), 41-53.

Becker, D. A.; Anderson, D. L.; Lindstrom, R. M.; Greenberg, R. R.; Garrity, K. M.; Mackey, E. A. J. Radioanal. Nucl. Chem. 1994, 179(1), 149-54.

Johnson & Johnson Vision Care, Inc., Solutions for Ophthalmic Lenses Containing at Least One Silicone Containing Component, U.S. Appl. No. 10/080,941, filed Jun. 30, 2004.

* cited by examiner

ANTIMICROBIAL LENSES, PROCESSES TO PREPARE THEM AND METHODS OF THEIR USE

RELATED APPLICATIONS

This patent application a continuation-in-part of application Ser. No. 10/715,903, filed Nov. 18, 2003.

FIELD OF THE INVENTION

This invention relates to packaging solutions that minimize the loss of inorganic additives present in a contact lens.

BACKGROUND OF THE INVENTION

Contact lenses have been used commercially to improve vision since the 1950s. The first contact lenses were made of hard materials. They were used by a patient during waking hours and removed for cleaning. Current developments in the field gave rise to soft contact lenses, which may be worn continuously, for several days or more without removal for cleaning. Although many patients favor these lenses due to their increased comfort, these lenses can cause some adverse reactions to the user. The extended use of the lenses can encourage the buildup of bacteria or other microbes, particularly, *Pseudomonas aeruginosa,* on the surfaces of soft contact lenses. The build-up of bacteria and other microbes can cause adverse side effects such as contact lens acute red eye and the like. Contact lenses comprising antimicrobial metal salts have been disclosed for preventing or retarding bacterial and microbial buildup. However, for these lenses to be effective commercially, it is necessary for the amount of antimicrobial metal salt in the lens to be consistent from lot to lot.

DETAILED DESCRIPTION OF THE INVENTION

The present invention relates to a packaging solution for packaging an ophthalmic device comprising at least one antimicrobial metal salt having a $K_{sp}$ of less than about $10^{-10}$ wherein said solution is substantially free from packaging solution salts which have anions, which when combined with said antimicrobial metal, form a salt having a $K_{sp}$ of less than about $10^{-6}$. When packaged in solutions of the present invention, the contact lenses comprising antimicrobial metal salts maintain a consistent level of antimicrobial metal salt.

As used herein, the term "ophthalmic device" refers to a device that resides in or on the eye. These devices can provide optical correction, wound care, drug delivery, diagnostic functionality, cosmetic enhancement or effect or a combination of these properties. The term lens includes but is not limited to soft contact lenses, hard contact lenses, intraocular lenses, overlay lenses, ocular inserts, and optical inserts and the like.

As used herein, the term, "antimicrobial metal salt" means a salt that when incorporated into an ophthalmic device imparts to the ophthalmic device one or more of the following properties, the inhibition of the adhesion of bacteria or other microbes to the device, the inhibition of the growth of bacteria or other microbes on the device, and the killing of bacteria or other microbes on the surface of the device or in an area surrounding the device. For purposes of this invention, adhesion of bacteria or other microbes to the device, the growth of bacteria or other microbes on the device and the presence of bacteria or other microbes on the surface of the device are collectively referred to as "microbial colonization." Preferably, the lenses exhibit a reduction of viable bacteria or other microbe of at least about 0.25 log, more preferably at least about 0.5 log, most preferably at least about 1.0 log ($\geqq 90\%$ inhibition). Such bacteria or other microbes include but are not limited to those organisms found in the eye, particularly *Pseudomonas aeruginosa, Acanthamoeba* species, *Staphyloccus. aureus, E. coli, Staphyloccus epidermidis,* and *Serratia marcesens.*

As use herein, the term "metal salt" means any molecule having the general formula $[M]_a[X]_b$ wherein X contains any negatively charged ion, a is $\geqq 1$, b is $\geqq 1$ and M is any positively charged metal selected from, but not limited to, the following $Al^{+3}$, $Co^{+2}$, $Co^{+3}$, $Ca^{+2}$, $Mg^{+2}$, $Ni^{+2}$, $Ti^{+2}$, $Ti^{+3}$, $Ti^{+4}$, $V^{+2}$, $V^{+3}$, $V^{+5}$, $Sr^{+2}$, $Fe^{+2}$, $Fe^{+3}$, $Ag^{+2}$, $Ag^+$, $Au^{+2}$, $Au^{+3}$, $Au^{+1}$, $Pd^{+2}$, $Pd^{+4}$, $Pt^{+2}$, $pt^{+4}$, $Cu^{+1}$, $Cu^{+2}$, $Mn^{+2}$, $Mn^{+3}$, $Mn^{+4}$, $Zn^{+2}$, and the like. Examples of X include but are not limited to $CO_3^{-2}$, $NO_3^{-1}$, $PO_4^{-3}$, $Cl^{-1}$, $I^{-1}$, $Br^{-1}$, $S^{-2}$, $O^{-2}$, $C^{1-5}$alkylCO$_2^{-1}$ and the like. As used herein the term metal salts does not include zeolites, disclosed in WO03/011351, which is hereby incorporated by reference in its entirety. The preferred a is 1, 2, or 3. The preferred b is 1, 2, or 3. The preferred metals ions are $Mg^{+2}$, $Zn^{+2}$, $Cu^{+1}$, $Cu^{+2}$, $Au^{+2}$, $Au^{+3}$, $Au^{+1}$, $Pd^{+2}$, $Pd^{+4}$, $Pt^{+2}$, $Pt^{+4}$, $Ag^{+2}$, and $Ag^{+1}$. The particularly preferred metal ion is $Ag^{+1}$. Examples of suitable metal salts include but are not limited to manganese sulfide, zinc oxide, zinc sulfide, copper sulfide, and copper phosphate. Examples of silver salts include but are not limited to silver nitrate, silver sulfate, silver iodate, silver carbonate, silver phosphate, silver sulfide, silver chloride, silver bromide, silver iodide, and silver oxide. The preferred silver salts are silver iodide, silver chloride, and silver bromide. It is preferred that the diameter of the metal salt particles is less than about ten microns (10 μm), more preferably less than about 5 μm, most preferably equal to or less than about 200 nm.

The $K_{sp}$; or solubility product constant is the product of the equilibrium constant K, and the concentration of solid salt in solution. $K_{sp}$ values for a number of salts are published in CRC Handbook of Chemistry and Physics, 78$^{th}$ Edition, CRC Press, Boca Raton Fla., 1997-99, pages 8-106 through 8-109). For example, if the metal salt is silver carbonate ($Ag_2CO_3$), the $K_{sp}$ is expressed by the following equation $$Ag_2CO_3(s) \rightarrow 2Ag^+(aq) + CO_3^{2-}(aq)$$

The $K_{sp}$ is calculated as follows

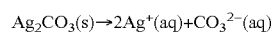

$$K_{sp} = [Ag^+]^2[CO_3^{2-}]$$

It has been discovered that if a contact lens comprising at least one antimicrobial metal salt having a $K_{sp}$ of less than about $10^{-10}$ is packaged in a solution which is substantially free from salts having anions which when combined with said antimicrobial metal form a salt having a $K_{sp}$ of more than about $10^{-6}$, little of the antimicrobial metal salt is lost during autoclaving and storing the lens. Preferably the lenses lose less than about 30% by weight of the antimicrobial salt and preferably less than about 20% by weight during autoclaving and storing. More preferably, upon repeated autoclaving, at least two autoclaving cycles, and up to five autoclaving cycles, the loss of the antimicrobial salt is less than about 15%.

Preferably the $K_{sp}$ of the salt formed from said antimicrobial metal and packaging solution salt anion is more than about $10^{-6}$ and the $K_{sp}$ of the antimicrobial metal salt is less than about $10^{-12}$. In another embodiment, the difference between the $K_{sp}$ of the antimicrobial metal salt and the salt formed from said antimicrobial metal and the packaging solution salt anion (or $\Delta K_{sp}$) is at least about six orders of magnitude, preferably at least about seven orders of magnitude and more preferably at least about eight orders of magnitude. Combinations of antimicrobial metal and packing solutions salts wherein the $\Delta K_{sp}$ is less than about 6 orders of magnitude may be used so long as the quantity of the salt in the packing solution is low enough that loss upon repeated autoclaving is less than about 15%.

In one embodiment, the solution may be any water-based solution that is used for the packaging, storage and/or cleaning of contact lenses, so long as the $K_{sp}$ of the salt formed from the antimicrobial metal and the packaging solution salt anion meets the requirements specified herein. Typical solutions include, without limitation, saline solutions, buffered solutions, buffered saline solutions and deionized water. The preferred aqueous solution is borate buffered solution containing salts including, without limitation, sodium sulfate, sodium lactate, sodium citrate, sodium chloride, mixtures thereof and the like.

In one embodiment of the present invention the packaging solution also has an osmolality of about 220 mOsm/kg or greater and preferably of about 230 mOsm/kg or greater.

Osmolality is a measure of the number of particles present in solution and is independent of the size or weight of the particles. It can be measured only by use of a property of the solution that is dependent only on the particle concentration. These properties are collectively referred to as Colligative Properties (vapor pressure depression, freezing point depression, boiling point elevation, osmotic pressure). Osmolality of a solution is the number of osmoles of solute per kilogram of solvent. This is the amount of a substance that yields, in ideal solution, that number of particles (Avogadro's number) that would depress the freezing point of the solvent by 1.86K. The osmolality values reported in the Examples were measured via freezing point depression using a Micro-Osmometer Model 3 MOplus. Solutions having the osmolility specified herein may be readily prepared by incorporating appropriate amounts of ionic salts, such as those listed herein. A suitable concentration range for the salt(s) are between about 0.01 to about 5 weight % and preferably between about 0.1 to about 3.0 weight % as part of a buffer system (such as borate or phosphate).

In another embodiment the packaging solution also has a conductivity of at least about 4 mS/cm or greater, and preferably at least about 5 mS/cm or greater. Conductivity is the ability of a material to conduct electric current. Conductivity may be measured using commercial conductivity probes. Solutions having the desired conductivities may be made by incorporating the salts listed herein. Salts which are more conductive, such as, for example sodium chloride, may be used in lesser quantities than salts with relatively low conductivities such as sodium borate.

In a further embodiment solutions of the present invention comprise an osmolality of at least about 220 mOsm/kg and a conductivity of at least about 4 mS/cm., preferably an osmolality of at least about 220 mOsm/kg and a conductivity of at least about 5 mS/cm., more preferably an osmolality of at least about 230 mOsm/kg and a conductivity of at least about 4 mS/cm., and most preferably an osmolality of at least about 230 mOsm/kg and a conductivity of at least about 5 mS/cm.

The solutions of the present invention may also comprise any known active and carrier components useful for lens packaging solution. Suitable active ingredients for lens packaging solutions include, without limitation, antibacterial agents, anti-dryness agents, such as polyvinyl alcohol, polyvinylpyrrolidone, dextran, polyethylene oxides, hydroxy propylmethyl cellulose (HPMC), tonicity agents, pharmaceuticals, nutraceuticals, additives which prevent the lens from sticking to the package and the like, and combinations thereof.

To form the solution, the ingredients are combined with the water-based solution, stirred, and dissolved. The pH of the solution preferably is adjusted to about 6.2 to about 7.7. The lens to be stored in the packaging solution of the invention is immersed in the solution and the solution and lens placed in the package in which the lens is to be stored. Alternatively, the solution may be placed into the package and the lens then placed into the solution. Typically, the package is then sealed by any convenient method, such as by heat sealing, and undergoes a suitable sterilization procedure.

Soft contact lenses may be made from any hydrophilic hydrogel or silicone elastomer or hydrogel materials, which include but are not limited to silicone hydrogels, and fluorohydrogels. Examples of soft contact lenses formulations include but are not limited to the formulations of etafilcon A, genfilcon A, lenefilcon A, polymacon, acquafilcon A, balafilcon A, galyfilcon A, senofilcon A and lotrafilcon A, and the like. The preferable contact lens formulations are etafilcon A, balafilcon A, acquafilcon A, lotrafilcon A, galyfilcon A, senofilcon A and silicone hydrogels, as prepared in U.S. Pat. No. 5,998,498, U.S. Ser. No. 09/532,943, a continuation-in-part of U.S. patent application Ser. No. 09/532,943, filed on Aug. 30, 2000, WO03/22321, U.S. patent application Ser. No. 6,087,415, U.S. 2002/0016383, JP 2001-188181, JP 2001-201723, JP 2001-183502, JP 2002-327063, U.S. Pat. No. 5,760,100, U.S. Pat. No. 5,776,999, U.S. Pat. No. 5,789,461, U.S. Pat. No. 5,849,811, and U.S. Pat. No. 5,965,631. These patents as well as all other patent disclosed herein are hereby incorporated by reference in their entirety.

Hard contact lenses are made from polymers that include but are not limited to poly(methyl)methacrylate, polymers of silicon acrylates, silicone acrylates, fluoroacrylates, fluoroethers, polyacetylenes, and polyimides, where the preparation of representative examples may be found in U.S. Pat. No. 4,330,383. Intraocular lenses of the invention can be formed using known materials. For example, the lenses may be made from a rigid material including, without limitation, polymethyl methacrylate, polystyrene, polycarbonate, or the like, and combinations thereof. Additionally, flexible materials may be used including, without limitation, hydrogels, silicone materials, acrylic materials, fluorocarbon materials and the like, or combinations thereof. Typical intraocular lenses are described in WO 0026698, WO 0022460, WO 9929750, WO 9927978, WO 0022459, U.S. Pat. Nos. 4,301,012; 4,872,876; 4,863,464; 4,725,277 and 4,731,079.

Additionally, suitable contact lenses may be formed from reaction mixtures comprising at least one silicone containing component. A silicone-containing component is one that contains at least one [—Si—O—Si] group, in a monomer, macromer or prepolymer. Preferably, the Si and attached O are present in the silicone-containing component in an amount greater than 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, N-vinyl lactam, N-vinylamide, and styryl functional groups. Examples of silicone components which may be included in the silicone hydrogel formulations include, but are not limited to silicone macromers, prepolymers and monomers. Examples of silicone macromers include, without limitation, polydimethylsiloxane methacrylated with pendant hydrophilic groups as described in U.S. Pat. Nos. 4,259,467; 4,260,725 and 4,261,875; polydimethylsiloxane macromers with polymerizable functional group(s) described in U.S. Pat. Nos. 4,136,250; 4,153,641; 4,189,546; 4,182,822; 4,343,927; 4,254,248; 4,355,147; 4,276,402; 4,327,203; 4,341,889; 4,486,577; 4,605,712; 4,543,398; 4,661,575; 4,703,097; 4,837,289; 4,954,586; 4,954,587; 5,346,946; 5,358,995; 5,387,632; 5,451,617; 5,486,579; 5,962,548; 5,981,615; 5,981,675; and 6,039,913; polysiloxane macromers incorporating hydrophilic monomers such as those described in U.S. Pat. Nos. 5,010,141; 5,057,578; 5,314,960; 5,371,147 and 5,336,797; macromers comprising polydimethylsiloxane blocks and polyether blocks such as those described in U.S. Pat. Nos. 4,871,785 and 5,034,461, combinations thereof and the like.

The silicone and/or fluorine containing macromers described in U.S. Pat. Nos. 5,760,100; 5,776,999; 5,789,461; 5,807,944; 5,965,631 and 5,958,440 may also be used. Suitable silicone monomers include tris(trimethylsiloxy)silylpropyl methacrylate, hydroxyl functional silicone containing monomers, such as 3-methacryloxy-2-hydroxypropyloxy) propylbis(trimethylsiloxy)methylsilane and those disclosed in WO03/22321, and mPDMS containing or the siloxane monomers described in U.S. Pat. Nos. 4,120,570, 4,139,692, 4,463,149, 4,450,264, 4,525,563; 5,998,498; 3,808,178; 4,139,513; 5,070,215; 5,710,302; 5,714,557 and 5,908,906.

Additional suitable siloxane containing monomers include, amide analogs of TRIS described in U.S. Pat. No. 4,711,943, vinylcarbamate or carbonate analogs described in U.S. Pat. No. 5,070,215, and monomers contained in U.S. Pat. No. 6,020,445, monomethacryloxypropyl terminated polydimethylsiloxanes, polydimethylsiloxanes, 3-methacryloxypropylbis(trimethylsiloxy)methylsilane, methacryloxypropylpentamethyl disiloxane and combinations thereof.

Suitable hydrophilic components are well known in the art and are disclosed in WO 2003/022321. Preferred hydrophilic monomers which may be incorporated into the polymer of the present invention include hydrophilic monomers such as N,N-dimethyl acrylamide (DMA), 2-hydroxyethyl acrylate, glycerol methacrylate, 2-hydroxyethyl methacrylamide, N-vinylpyrrolidone (NVP), HEMA, and polyethyleneglycol monomethacrylate. Most preferred hydrophilic monomers include DMA, NVP, HEMA and mixtures thereof. Polymeric wetting agents and compatibilzing components may also be included. As used herein, "polymeric wetting agent" refers to substances having a weight average molecular weight of at least about 2,500 Daltons. The preferred weight average molecular weight of these polymeric wetting agents is greater than about 100,000; more preferably between about 150,000 to about 2,000,000 Daltons, more preferably still between about 300,000 to about 1,800,000 Daltons. Alternatively, the molecular weight of polymeric wetting agents can be also expressed by the K-value, based on kinematic viscosity measurements, as described in Encyclopedia of Polymer Science and Engineering, N-Vinyl Amide Polymers, Second edition, Vol 17, pgs. 198-257, John Wiley & Sons Inc. When expressed in this manner, hydrophilic monomers having K-values of greater than about 12 and preferably between about 30 and about 150.

The way in which the polymeric wetting agent is added to the lens is not critical. The polymeric wetting agent may be added to the reaction mixture as a polymer, may be formed from at least one hydrophilic monomer which is added to the reaction mixture and forms a hydrophilic polymer upon curing of the reaction mixture or may be added after the lens is formed in the packaging solution. Examples of polymeric wetting agents include but are not limited to polymers and copolymers comprising polyamides, polylactones, polyimides, polylactams and functionalized polyamides, polylactones, polyimides, polylactams, such as DMA functionalized by copolymerizing DMA with a lesser molar amount of a hydroxyl-functional monomer such as HEMA, and then reacting the hydroxyl groups of the resulting copolymer with materials containing radical polymerizable groups, such as isocyanatoethylmethacrylate or methacryloyl chloride. Hydrophilic prepolymers made from DMA or n-vinyl pyrrolidone with glycidyl methacrylate may also be used. The glycidyl methacrylate ring can be opened to give a diol which may be used in conjunction with other hydrophilic prepolymer in a mixed system to increase the compatibility of the high molecular weight hydrophilic polymer, hydroxyl-functionalized silicone containing monomer and any other groups which impart compatibility. Polymeric wetting agents include but are not limited to those disclosed in U.S. Pat. No. 6,367,929, WO 2003/022321 and acyclic polyamides comprising repeating units of Formula

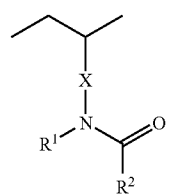

I

Wherein X is a direct bond,

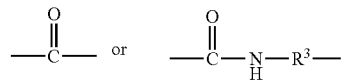

wherein $R^3$ is a C1 to C3 alkyl group;
$R^1$ is selected from H, straight or branched, substituted or unsubstituted C1 to C4 alkyl groups,
$R^2$ is selected from H, straight or branched, substituted or unsubstituted C1 to C4 alkyl groups, amino groups having up to two carbons, amide groups having up to four carbon atoms and alkoxy groups having up to two carbons and wherein the number of carbon atoms in R1 and R2 taken together is 8 or less, and preferably 6 or less. Homopolymers and copolymers comprising N-vinylpyrrolidone, N-vinyl-N-methylacetamide, (meth)acrylic acid, N, N-dimethylacrylamide, combinations thereof and the like are particularly preferred.

In certain embodiments a hydroxyl containing component may also be included. The hydroxyl containing component that may be used to make the polymers of this invention have at least one polymerizable double bond and at least one hydroxyl group. Examples of polymerizable double bonds include acrylic, methacrylic, acrylamido, methacrylamido, fumaric, maleic, styryl, isopropenylphenyl, O-vinylcarbonate, O-vinylcarbamate, allylic, O-vinylacetyl and N-vinyllactam and N-vinylamido double bonds. The hydroxyl containing component may also act as a crosslinking agent. The hydroxyl group may be a primary, secondary or tertiary alcohol group, and may be located on an alkyl or aryl group. Examples of hydroxyl containing monomers that may be used include but are not limited to 2-hydroxyethyl methacrylate ("HEMA"), 2-hydroxyethyl acrylate, 2-hydroxyethyl methacrylamide, 2-hydroxyethyl acrylamide, N-2-hydroxyethyl vinyl carbamate, 2-hydroxyethyl vinyl carbonate, 2-hydroxypropyl methacrylate, hydroxyhexyl methacrylate, hydroxyoctyl methacrylate and other hydroxyl functional monomers as disclosed in U.S. Pat. Nos. 5,006,622; 5,070,215; 5,256,751 and 5,311,223. Preferred hydroxyl containing components include 2-hydroxyethyl methacrylate.

In addition, the lens may also include cross-linkers, photoinitiators, UV absorbers, medicinal agents, antimicrobial compounds, reactive tints, pigments, copolymerizable and nonpolymerizable dyes, release agents, combinations thereof and the like. These additional components may be incorporated into the lens in any way, such as, but not limited to polymerized into the lens matrix, admixed into the monomer mix used to make the lens or absorbed into the lens.

The contact lenses may be coated to increase their compatibility with living tissue with a number of agents that are used to coat lens. For example, the coating procedures, compositions, and methods of WO03/11551, U.S. Pat. Nos. 6,087,415, 5,779,943, 5,275,838, 4,973,493, 5,135,297, 6,193,369, 6,213,604, 6,200,626, and 5,760,100 may be used and these applications and patents are hereby incorporated by reference for those procedures, compositions, and methods.

The amount of antimicrobial metal in the lenses is measured based upon the total weight of the lenses. When the antimicrobial metal is silver, the preferred amount of silver is about 0.00001 weight percent (0.1 ppm) to about 10.0 weight percent, preferably about 0.0001 weight percent (1 ppm) to about 1.0 weight percent, most preferably about 0.001 weight percent (10 ppm) to about 0.1 weight percent, based on the dry weight of the lens. With respect to adding metal salts, the molecular weight of the metal salts determines the conversion of weight percent of metal ion to metal salt. The preferred amount of silver salt is about 0.00003 weight percent (0.3 ppm) to about 30.0 weight percent, preferably about 0.0003 weight percent (3 ppm) to about 3.0 weight percent, most preferably about 0.003 weight percent (30 ppm) to about 0.3 weight percent, based on the dry weight of the lens.

The preferred antimicrobial metal salts of this invention are silver iodide, silver chloride and silver bromide, where silver iodide is particularly preferred.

The term "forming" refers to any of a number of methods used to form lenses that include but are not limited to curing with light or heat. The lens formulations of the present invention can be formed by any of the methods know to those skilled in the art, such as shaking or stirring, and used to form polymeric articles or devices by known methods.

Metal salts of the invention may be added (prior to curing) to the soft contact lens formulations described in U.S. Pat. No. 5,710,302, WO 9421698, EP 406161, JP 2000016905, U.S. Pat. No. 5,998,498, U.S. patent application Ser. No. 09/532,943, U.S. Pat. No. 6,087,415, U.S. Pat. No. 5,760,100, U.S. Pat. No. 5,776,999, U.S. Pat. No. 5,789,461, U.S. Pat. No. 5,849,811, and U.S. Pat. No. 5,965,631. In addition, metal salts of the invention may be added to the formulations of commercial soft contact lenses.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

The osmolality of a solution may be measured using a Micro-Osmometer Model 3 MOplus and the following procedure. The instrument was internally calibrated with NIST traceable 50 mOsm and 850 mOsm standards. The solutions to be tested were kept sealed in a vial until evaluation. The sampling system (a pipette fitted with a plunger) was rinsed by pipetting sample solution into the barrel of the sampling system and discarding. Solution was pipetted into the sample system, the sample system was placed in the osmometer and the osmolality was measured. The measurement was repeated three times and the average is reported.

The conductivity may be measured using a FISHER® ACCUMET® 150 and the following procedure. The instrument is calibrated using NIST traceable conductivity standards. The solutions to be tested were kept sealed in a vial until evaluation. About 30 ml of solution was placed in a hinged cap sample vial. The conductivity probe is dipped into the solution at least three times prior to sample evaluation to wet the probe and remove any bubbles. The conductivity probe and automatic temperature compensation probe are immersed in the sample solution and the conductivity is recorded when the reading on the instrument stabilizes.

Silver content of the lenses after lens autoclaving was determined by Instrumental Neutron Activation Analysis "INAA". INAA is a qualitative and quantitative elemental analysis method based on the artificial induction of specific radionuclides by irradiation with neutrons in a nuclear reactor. Irradiation of the sample is followed by the quantitative measurement of the characteristic gamma rays emitted by the decaying radionuclides. The gamma rays detected at a particular energy are indicative of a particular radionuclide's presence, allowing for a high degree of specificity. Becker, D. A.; Greenberg, R. R.; Stone, S. F. J. Radioanal. Nucl. Chem. 1992, 160(1), 41-53; Becker, D. A.; Anderson, D. L.; Lindstrom, R. M.; Greenberg, R. R.; Garrity, K. M.; Mackey, E. A. J. Radioanal. Nucl. Chem. 1994, 179(1), 149-54. The INAA procedure used to quantify silver content in contact lens material uses the following two nuclear reactions:

1. In the activation reaction, $^{110}$Ag is produced from stable $^{109}$Ag (isotopic abundance=48.16%) after capture of a radioactive neutron produced in a nuclear reactor.
2. In the decay reaction, $^{110}$Ag ($\tau^{1/2}$=24.6 seconds) decays primarily by negatron emission proportional to initial concentration with an energy characteristic to this radionuclide (657.8 keV).

The gamma-ray emission specific to the decay of $^{110}$Ag from irradiated. standards and samples are measured by gamma-ray spectroscopy, a well-established pulse-height analysis technique, yielding a measure of the concentration of the analyte.

EXAMPLES

The following abbreviations were used in the examples

Blue HEMA=the reaction product of reactive blue number 4 and HEMA, as described in Example 4 or U.S. Pat. No. 5,944,853

CGI 1850=1:1 (w/w) blend of 1-hydroxycyclohexyl phenyl ketone and bis (2,6-dimethyoxybenzoyl)-2,4-4-trimethylpentyl phosphine oxide DI water=deionized water D3O=3,7-dimethyl-3-octanol DMA=N,N-dimethylacrylamide HEMA=hydroxyethyl methacrylate IPA=Isopropyl alcohol Macromer=a macromer made according to Example 14, herein MC=methyl ether cellulose mPDMS=mono-methacryloxypropyl terminated polydimethylsiloxane (MW 800-1000)

Norbloc=2-(2'-hydroxy-5-methacrylyloxyethylphenyl)-2H-benzotriazole ppm=parts per million micrograms of sample per gram of dry lens
PVP=polyvinylpyrrolidinone (K 90)
Simma 2=3-methacryloxy-2-hydroxypropyloxy)propyl-bis (trimethylsiloxy)methylsilane
BBPS=borate buffered packaging solution
SSPS=borate buffered sodium sulfate packaging solution
TEGDMA=tetraethyleneglycol dimethacrylate
w/w=weight/total weight
w/v=weight/total volume
v/v=volume/total volume
The following solutions were prepared for use Borate Buffered Packaging Solution (BBPS)

A solution was made by adding 0.185 weight % of sodium borate, 0.926 weight % boric acid and 98.89 weight % water into a volumetric flask and was mixed at ambient temperature until all solids were dissolved. Properties for the BBPS are listed in Table 1, below.

Borate Buffered Saline Solution (BBSS)

A solution was made by adding 0.185 g of sodium borate, 0.926 g boric acid, 0.847 g sodium chloride and 100 mL water into a flask and was mixed at ambient temperature until all solids were dissolved. Properties for the BBSS are listed in Table 1, below Borate Buffered Sodium Sulfate Packaging Solution (SSPS)

A solution was made by adding 0.185 weight % of sodium borate, 0.926 weight % boric acid, 1.4 weight % of sodium sulfate and 97.49 weight % water into a volumetric flask and was mixed at ambient temperature until all solids were dissolved. Properties for the SSPS are listed in Table 1, below.

Borate Buffered Packaging Solution with 400 uL of Packing Soln. (spiked)

A solution was made by adding 0.15 weight % of sodium borate, 0.92 weight % boric acid, 0.35% sodium chloride, 0.004% EDTA and 98.58 weight % water into a volumetric flask and was mixed at ambient temperature until all solids were dissolved. Properties for the special packing solution are listed in Table 1. below.

TABLE 1

Solution Properties

| Properties | BBPS | BBSS | SSPS | Spiked |
|---|---|---|---|---|
| PH | 7.59 (0) | 7.52 | 7.52 (0) | 7.50 (0) |
| Osmolality (mOsm/kg)(std) | 163 (0) | 417 | 382 (0.5) | 273 (0) |
| Conductivity (m S/cm) | 0.7 (0) | 14.6 | 15.3 (0.2) | 6.8 (0) |
| Ksp (Ag/solution anion) | $(Ag_2B_4O_7)$ | $1.77 \times 10^{-10}$ (AgCl) | $1.2 \times 10^{-5}$ (AgSO$_4$) | $1.77 \times 10^{-10}$ (AgCl) |

Example 1

A monomer mix is made by mixing 77 weight % of the monomers listed in Table 2 with and 23% D3O.

TABLE 2

| Component | Wt % |
|---|---|
| SiMAA2 | 28 |
| MPDMS | 31 |
| DMA | 24 |
| HEMA | 6 |

TABLE 2-continued

| Component | Wt % |
|---|---|
| PVP | 7 |
| Norbloc | 2 |
| Blue HEMA | 0.02 |
| CGI 1850 | 0.48 |
| TEGDMA | 1.5 |

Contact lenses were made by placing the monomer mix into thermoplastic contact lens molds, and irradiating using Philips TL20W/03T fluorescent bulbs (intensity of about 1 mW/cm$^2$ for 8 minutes and about 4 mW/cm$^2$ for 4 minutes) at 45° C. The molds were opened and lenses were extracted into IPA solvent to insure removal of residual diluent and monomers. The lenses were then rinsed in a 50 ppm methyl cellulose in DI mixture to insure removal of solvent. The lenses were then equlibrated in deionized water.

Examples 2-13

Lenses made as in Example 1 were placed in a 300 ppm sodium iodide solution overnight at room temperature. The lenses were immersed in a 150 ppm silver nitrate solution for 2-minutes at room temperature and then rinsed 2-times with DI water in 30-minute intervals to remove any excess silver. Three lenses were equilibrated in each of the solutions listed in Table 3, below. Each set of three contact lenses was packaged into three polypropylene blister packs containing the solutions shown in Table 3. The blister packs were heat sealed (225° C., 90 psi and 1.5 seconds). The blister packs containing the lenses were autoclaved at 121° C. for 30 minutes, and allowed to cool to room temperature. The number of autoclave cycles each set of blister packs was exposed to is listed in Table 3. Each lens was analyzed for residual silver content after the noted number of autoclave cycles. The results are shown in Table 3, below.

TABLE 3

| Ex. # | Solution | # cycles | [Ag] (μg)* |
|---|---|---|---|
| 2 | BBPS | 1 | 4.37 (0.11) |
| 3 | BBPS | 3 | 4.52 (0.06) |
| 4 | BBPS | 5 | 4.57 (0.22) |
| 5 | BBPS | 8 | 4.57 (0.07) |
| 6 | SSPS | 1 | 3.3 (0.2) |
| 7 | SSPS | 3 | 3.4 (0.3) |
| 8 | SSPS | 5 | 3.4 (0.1) |
| 9 | SSPS | 8 | 3.4 (0.2) |
| 10 | Spiked | 1 | 3.3 (0.1) |
| 11 | Spiked | 3 | 2.4 (0.1) |
| 12 | Spiked | 5 | 1.9 (0.9) |
| 13 | Spiked | 8 | 1.7 (0.1) |

*standard deviations shown in parenthesis

Example 14

The following ingredients were combined using the steps below to generate Macromer.

TABLE 4

| Chemical | Weight (g) or volume (ml) |
|---|---|
| Bis(dimethylamino)-methylsilane | 5.72 g |
| 1.0 M Solution of tetrabutylammonium 3-chlorobenzoate (TBACB) in THF | 2.6 ml |

TABLE 4-continued

| Chemical | Weight (g) or volume (ml) |
|---|---|
| p-xylene | 15.83 g |
| MMA | 29.44 g |
| Bloc-HEMA | 361.16 g |
| THF | 840 g |
| Methyltrimethylsilyl dimethylketene acetal | 38.53 g |
| 0.4 M solution of tetrabutylammonium 3-chlorobenzoate (TBACB) in THF | 6 ml |
| Step 2 | |
| Bloc-HEMA | 89.23 g |
| MPDMS | 693.00 g |
| TRIS | 701.46 g |
| Bis(dimethylamino)-methylsilane | 3.81 g |
| Step 3 | |
| Solution of Bloc-HEMA | 361.16 g |
| MMA | 29.44 g |
| Bis(dimethylamino)-methylsilane | 1.92 g |
| THF | 270 g |
| Step 4 | |
| Water | 93.9 g |
| Methanol | 141.2 g |
| Dichloroacetic acid | 1.68 g |
| Step 5 | |
| 3-Isopropenyl-α,α-dimethylbenzyl isocyanate | 169.07 g |
| TEA | 1.18 g |

Bloc-HEMA, MMA, mPDMS (about 800 to about 1000 MW), TRIS, p-xylene and tetrahydrofuran (THF) were dried over preactivated 4A molecular sieve, and THF, mPDMS, and TRIS were passed through aluminum oxide column before use.

To a dry container in a dry box under nitrogen was added bis(dimethylamino)-methylsilane, a 1M solution of tetrabutylammonium 3-chlorobenzoate (TBACB) in THF, p-xylene, MMA (1.4 eqv. relative to initiator), Bloc-HEMA (8.5 eqv. relative to photoinitiator) and THF. The above mixture was charged to a dry flask equipped with a thermocouple and a condenser connected to a nitrogen source.

To the reaction mixture was injected methyltrimethylsilyl dimethylketene acetal while stirring and purging with nitrogen. The reaction was allowed to exotherm to about 65° C. and then after the temperature of the solution dropped, a solution of TBACB in dry THF (0.4 M) was fed in slowly throughout the rest of the reaction. Then in step 2, a mixture of Bloc-HEMA (2.1 eqv. to initiator), mPDMS (3.3 eqv. to initiator), TRIS (7.9 eqv. to initiator) and bis(dimethylamino)-methylsilane, prepared in dry box, was added under nitrogen. The reaction mixture was again allowed to exotherm to approximately 42° C. and then allowed to cool to 32° C. The solution was stirred at 32° C. by using a temperature controller and heating equipment for about five hours. In step 3, a mixture on of Bloc-HEMA (8.5 eqv. to initiator), MMA (1.4 eqv. relative to initiator) and bis(dimethylamino)-methylsilane was added and the whole mixture allowed to exotherm to 46-49° C. After the mixture reacted about two hours, 270 g of THF was added to reduce the viscosity and the solution was stirred for additional 30 minutes.

In step 4, a mixture of water, methanol and dichloroacetic acid was added and the mixture was refluxed for five hours to de-block the protecting groups. The solvents were then removed by distillation and toluene was added to aid in removal of residual water until a vapor temperature reached 110° C.

A solution of TMI and 1.2 mole % TEA relative to TMI was added to the above solution in toluene. The whole mixture was stirred at 110° C. for three hours and the disappearance of the isocyanate peak was monitored by IR. The toluene was removed under reduced pressure at around 45° C. to give a raw macromer.

Purification procedures were employed to remove high molecular weight species. The raw macromer was re-dissolved in acetone (2:1 w/w acetone to macromer) and the acetone solution was set overnight to allow high molecular weight species to separate. The top clear phase was filtered through a PTFE membrane by pressure filtration. The filtrate was slowly charged into water (4:1 v/v water to filtrate) and the macromer was precipitated out. The macromer was collected and dried using a vacuum oven at 45-65° C. under reduced pressure until there was no weight change.

Further purification to remove low molecular weight species was also done by re-precipitation of the Macromer from the mixture of acetone and acetonitrile (1:5 v/v).

Example 15

Sodium Iodide (3.2 mg Aldrich) was added to 15.0 g of a hydrogel blend made from the following (all amounts were calculated as weight percent of the total weight of the combination): 17.98% Macromer 5, 28.0% mPDMS, 14.0% TRIS, 26.0% DMA, 5.0% HEMA, 1.0% TEGDMA, 5.0% PVP, 2.0% Norbloc, 1.0% CGI 1850 and 0.02% Blue HEMA, 80 weight percent of the preceding component mixture was further diluted with diluent, 20 weight percent of D3O ("D3O Monomer Blend"). The mixture was sonicated for 1.5 hours at 30° C., and then stored in a heated oven @ 55° C. overnight. The monomer mix was degassed under vacuum for 30 minutes, and used to make lenses, utilizing Topas frames at 50-55° C. under Philips TL03 lamps with 30 minutes of irradiation.

Eight frames were manually demolded, and the lenses (obtained sticking to the back curve or front curve) were enclosed individually in hydration vehicles (Fisher brand, HistoPrep disposable plastic tissue capsules) and immersed in 2 L of DI water containing 447 mg AgNO$_3$. An orbital shaker was used to keep the solution agitated. After 2 hours, the lenses were removed from the hydration vehicles, and released from the molds in a jar containing 150 mL of silver nitrate solution (0.15 mg/mL in DI water) and 225 mL isopropyl alcohol. After 2 hours, the solution was replaced with 200 mL isopropanol, and the lenses were then stepped down using DI water/IPA mixtures by (4×40 mL) exchanges of the hydration solution with DI water, allowing the lenses to equilibrate 20-30 minutes between exchanges. The lenses were then transferred into DI water for a total of 4×75 mL washes of 20-30 minutes each. Lenses from the last DI water wash were stored in a 10 mL of fresh DI water. The lenses were autoclaved (each in 3.0 mL of Special Packing Solution). The final silver content in the lenses was determined by INAA to be 286±15 ppm (theoretical=189 ppm).

Example 16

Tetrabutylammonium Chloride (8.9 mg, Fluka) was added to 15.1 g of D3O Monomer Blend. The mixture was sonicated for 1 hour, rolled on a jar roller for a further 30 minutes, and then stored in a heated oven @ 55° C. overnight. The monomer mix was degassed under vacuum for 30 minutes, and used to make lenses, utilizing Topas frames at 50° C. under Philips TL03 lamps with 30 minutes of irradiation.

Ten frames of lenses were manually demolded, and the rings due to excess monomer were discarded. The lenses, obtained sticking to either the back curve or front curve, were loaded onto hydration trays, which were then immersed in 2.75 L of silver nitrate solution ('silverizing bath', 0.155 mg/mL in DI water). The silver nitrate solution was kept agitated by utilizing an orbital shaker. After 2 hours, the lenses were removed from the hydration trays, and placed in a jar containing 120 mL solution from the 'silverizing bath' and 180 mL isopropanol to release the lenses from the molds.

The released lenses were then further hydrated analogously to the procedure described in Example 15. The final silver content in the lenses was determined to be 331±7 ppm (theoretical=286 ppm). The average haze value for these lenses was 21.8±1.8% relative to CSI commercial standards.

Examples 17-20

Lenses made in Examples 15 and 16 were packaged in 3.0 mL glass vials half of the lenses of each lens type were packaged in BBPS and the other half were packaged in BBSS and sealed. The lenses were autoclaved one to three times at 121° C. for 30 minutes. The lenses were evaluated for silver content and the data is presented in Table 5, below.

TABLE 5

|  | 17 | 18 | 19 | 20 |
|---|---|---|---|---|
| Antimicrobial salt | AgCl | AgCl | AgI | AgI |
| Ksp - Antimicrobial salt | $1.77 \times 10^{-10}$ | $1.77 \times 10^{-10}$ | $8.52 \times 10^{-17}$ | $8.52 \times 10^{-17}$ |
| Solution | BBPS | BBSS | BBPS | BBSS |
| $[Ag]_{initial}$ | 342 (6) | 342 (6) | 286 (15) | 286 (15) |
| $[Ag]_{1\ cycle}$ | 180 (8) | 42 (5) | 233 (3) | 131 (4) |
| $[Ag]_{2\ cycle}$ | 164 (9) | 36 (3) | 236 (6) | 94 (6) |
| $[Ag]_{3\ cycle}$ | 179 (11) | 33 (6) | 239 (7) | 62 (4) |

Values in parentheses are standard deviations

What is claimed is:

1. A packaging solution for packaging an ophthalmic device comprising at least one antimicrobial metal salt having a $K_{sp}$ of less than about $10^{-10}$ wherein said solution has an osmolality of about 220 mOsm/kg or greater and is substantially free from packaging solution salts which have anions which when combined with a cation from said antimicrobial metal salt form a second salt, such that said ophthalmic device loses less than about 30% by weight of said antimicrobial metal salt during autoclaving and storage in said packaging solution.

2. The packaging solution of claim 1 wherein said packaging solution salts has an osmolality of about 230 mOsm/kg or greater.

3. The packaging solution of claim 1 wherein said packaging solution has a conductivity of at least about 4 mS/cm or greater.

4. The packaging solution of claim 1 wherein said packaging solution has a conductivity of at least about 5 mS/cm or greater.

5. The packaging solution of claim 1 wherein said ophthalmic device is a contact lens.

6. The packaging solution of claim 1 wherein said antimicrobial metal salt comprises at least one cation selected from the group consisting of $Al^{+3}$, $Co^{+2}$, $Co^{+3}$, $Ca^{+2}$, $Mg^{+2}$, $Ni^{+2}$, $Ti^{+2}$, $Ti^{+3}$, $Ti^{+4}$, $V^{+2}$, $V^{+3}$, $V^{+5}$, $Sr^{+2}$, $Fe^{+2}$, $Fe^{+3}$, $Ag^{+2}$, $Ag^{+}$, $Au^{+2}$, $Au^{+3}$, $Au^{+1}Pd^{+2}$, $Pd^{+4}$, $pT^{+2}$, $PT^{+4}$, $Cu^{+1}$, $Cu^{+2}$, $Mn^{+2}$, $Mn^{+3}$, $Mn^{+4}$, $Zn^{+2}$ and combinations thereof.

7. The packaging solution of claim 1 wherein said antimicrobial metal salt comprises at least one cation selected from the group consisting of $Mg^{+2}$, $Zn^{+2}$, $Cu^{+1}$, $Cu^{+2}$, $Au^{+2}$, $Au^{+3}$, $Au^{+1}$, $Pd^{+2}$, $Pd^{+4}$, $Pt^{+2}$, $Pt^{+4}$, $Ag^{+2}$, $Ag^{+1}$ and combinations thereof.

8. The packaging solution of claim 1 wherein said antimicrobial metal salt is a silver salt.

9. The packaging solution of claim 1 wherein said ophthalmic device loses less than about 20% by weight of the antimicrobial salt during autoclaving and storing.

10. The packaging solution of claim 1 wherein said ophthalmic device loses less than about 15% by weight of the antimicrobial salt after at least two autoclaving cycles.

11. A packaging solution for packaging an ophthalmic device comprising at least one antimicrobial metal salt having a $K_{sp}$ of less than about $10^{-10}$ wherein said solution has an osmolality of about 220 mOsm/kg or greater and is substantially free from packaging solution salts which have anions which when combined with a cation from said antimicrobial metal form a salt having a $K_{sp}$ which is less than about six orders of magnitude less that said $K_{sp}$ of said antimicrobial metal salt and said antimicrobial metal salt is present in a concentration sufficient to provide loss of said antimicrobial metal salt from said ophthalmic device upon autoclaving of less than about 15%.

* * * * *

UNITED STATES PATENT AND TRADEMARK OFFICE
CERTIFICATE OF CORRECTION

| | |
|---|---|
| PATENT NO. | : 7,416,737 B2 |
| APPLICATION NO. | : 10/882072 |
| DATED | : August 26, 2008 |
| INVENTOR(S) | : Nayiby Alvarez-Carrigan et al. |

It is certified that error appears in the above-identified patent and that said Letters Patent is hereby corrected as shown below:

Col. 14, line 19, kindly delete "$pT^{+2}, PT^{+4}$" and insert --$Pt^{+2}, Pt^{+4}$--

Signed and Sealed this

Fourteenth Day of July, 2009

JOHN DOLL
*Acting Director of the United States Patent and Trademark Office*